United States Patent [19]

Briggs

[11] Plant 4,539

[45] May 27, 1980

[54] TOMATO PLANT

[75] Inventor: Carroll G. Briggs, San Juan Bautista, Calif.

[73] Assignee: The Upjohn Company, Kalamazoo, Mich.

[21] Appl. No.: 968,072

[22] Filed: Dec. 11, 1978

[51] Int. Cl.[2] ..... A01H 5/00

[52] U.S. Cl. ..... Plt./89

[58] Field of Search ..... Plt./89

*Primary Examiner*—Robert E. Bagwill

*Attorney, Agent, or Firm*—Sidney B. Williams, Jr.

[57] ABSTRACT

A new and distinct variety of a hybrid tomato plant substantially as herein shown and described, characterized as to novelty when compared to Walter, the most similar variety to it, by uniform crop characteristics, low grading loss, high yield, early maturity, low percentage of fruit with stems, low percentage of fruit ripening defects, multiple disease resistance and tolerance.

1 Drawing Figure

BACKGROUND OF THE INVENTION

The present invention relates to a new and distinct variety of tomato plant which was produced and propagated asexually by Carroll G. Briggs. The plant was propagated by crossing the variety TOM 536 with TOM 540. The former being the seed parent and the latter being the pollen parent.

Their breeding has produced a new and improved variety of tomato plant which is distinguished from its parents as well as the variety most similar to it, Walter, by uniform crop characteristic, low grading loss, high yield, low percentage of fruit with stems, low percentage of fruit ripening defects, multiple disease resistance and tolerance.

DRAWINGS

In the drawing, which is a photographic illustration of the new variety, is a view of the leaves and fruit.

DETAILED DESCRIPTION

A detailed description of my new variety is as follows based upon observation made from plants and fruit grown in California, Florida, the Northeastern and Southeastern United States and Italy.

Type: Determinate market tomato.

Breeding: Seedling.

*Seed parent.*—TOM 536.

*Pollent parent.*—TOM 540.

Propagation: Holds its distinguishing characteristics through succeeding propagation by cuttings.

Plant:

*Habit.*—Determinate in growth habit. Suitable for use as a ground or staked variety. Vines — hardy and vigorous.

*Growth.*—Slightly smaller and more compact than Walter and with relatively shorter internodes. More concentrated than Walter.

*Foliage.*—Leaves — usually compound of 11–12 leaflets when mature. Leaflets: Shape — pointed oval in general. Size (mature) — length from about 2¾ inches to 4¼ inches; width from about 1¾ inches to 2¾ inches. Color — dark green similar to Walter.

*Main stems.*—Branches — 6–8 branches from main stem. New shoots — 5–7 new shoots per branch.

Fruit:

*Borne.*—Heavily; usually from 29 to 47 fruits per plant.

*Shape.*—Deep to slightly flattened globe.

*Size.*—Heavy; average weight of 0.3 pounds. Length — from about 2¾ inches to 2½ inches. Width — from about 2¾ inches to 2¼ inches. Height — from about 2½ inches to 2¾ inches. Similar to Walter but slightly larger.

*Texture.*—Thick meated.

*Color.*—Immature — surface uniform light green with smooth, even, waxy appearance; shoulders smooth, dark green. Mature — medium red without streaking or yellow shoulders colors of immature and mature fruit similar to Walter.

*Bearing season.*—About 7 to 10 days earlier than Walter, beginning between 115 and 125 days from planting of cuttings, depending on seasonal conditions.

*Flavor.*—Similar to Walter.

*Skin.*—Relatively tough.

Disease resistance: Resistant to Fusarium Wilt-*Fusarium oxysporum F. lycopersici* (Race 1 and Race 2), Gray leaf spot-Stemphylum solani, and Alternaria stem canker — *Alternaria, alternia fs lycopersici* which became infected under the same cultural conditions as grown in California and Southeastern United States.

Drought resistance: Good as determined in the same manner as disease resistance.

Use: Market fruit for human consumption.

I claim:

1. A new and distinct variety of a hybrid tomato plant substantially as herein shown and described, characterized as to novelty by uniform crop characteristics, low grading loss, high yields, low percentage of fruit with stems, low percentage of fruit ripening defects, multiple disease resistance and tolerance.

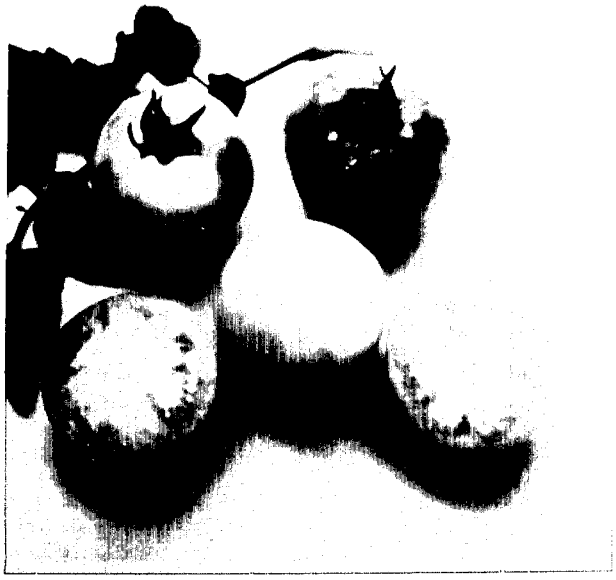

* * * * *